(12) United States Patent
Yu

(10) Patent No.: US 10,490,298 B2
(45) Date of Patent: Nov. 26, 2019

(54) SIMULATION APPARATUS AND METHOD FOR INTRACELLULAR RESPONSES

(71) Applicant: KOREA INSTITUTE OF SCIENCE AND TECHNOLOGY INFORMATION, Daejeon (KR)

(72) Inventor: Seok Jong Yu, Cheongju-si (KR)

(73) Assignee: KOREA INSTITUTE OF SCIENCE AND TECHNOLOGY INFORMATION, Daejeon (KR)

( * ) Notice: Subject to any disclaimer, the term of this patent is extended or adjusted under 35 U.S.C. 154(b) by 552 days.

(21) Appl. No.: 15/241,092

(22) Filed: Aug. 19, 2016

(65) Prior Publication Data

US 2017/0076021 A1 Mar. 16, 2017

(30) Foreign Application Priority Data

Sep. 11, 2015 (KR) .......................... 10-2015-0129167

(51) Int. Cl.
*G16B 5/00* (2019.01)
(52) U.S. Cl.
CPC ..................................... *G16B 5/00* (2019.02)
(58) Field of Classification Search
CPC ....................................................... G16B 5/00
USPC ........................................................... 702/19
See application file for complete search history.

(56) References Cited

FOREIGN PATENT DOCUMENTS

| JP | 2002-007380 A | 1/2002 |
|----|---------------|--------|
| JP | 2003-505749 A | 2/2003 |
| JP | 2004-129626 A | 4/2004 |
| JP | 2004-533037 A | 10/2004 |
| JP | 2005-229805 A | 9/2005 |
| JP | 2007-047994 A | 2/2007 |
| JP | 2013-169291 A | 9/2013 |

OTHER PUBLICATIONS

Rui Yamagushi, Tomoyuki Higuchi, "State space model approach to analyse cDNA microarray time course data of yeast", IPSJ SIG Technical Reports, Dec. 22, 2005, 67-73 pages, vol. 2005, No. 128, ISSN 0919-6072.

*Primary Examiner* — Jerry Lin
(74) *Attorney, Agent, or Firm* — Park, Kim & Suh, LLC

(57) ABSTRACT

Disclosed is an apparatus and method for various intracellular responses throughout the life cycle of cells. The simulation apparatus for intracellular responses, includes a database configured to include information regarding cells for cell model generation, a model generation module configured to receive the information regarding cells from the database and to generate a cell model, an expression module configured to receive the information regarding cells from the database and to construct a numerical model for protein quantification, and a simulation module configured to allocate intracellular responses in the generated cell model to at least one computer and to simulate the intracellular responses.

14 Claims, 3 Drawing Sheets

SIMULATION APPARATUS AND METHOD FOR INTRACELLULAR RESPONSES

CROSS-REFERENCE TO RELATED APPLICATIONS

This application claims priority to and the benefit of Korean Patent Application No. 10-2015-0106630 filed in the Korean Intellectual Property Office on Sep. 11, 2015, the entire contents of which are incorporated herein by reference.

BACKGROUND OF THE INVENTION

Field of the Invention

The present invention relates to a simulation apparatus and method for intracellular responses, and more particularly, to a 3D simulation apparatus and method for various intracellular responses using gene expression information.

Discussion of the Related Art

As research on system biology is vigorously carried out, information regarding chemical substances constituting a living body, such as ions, proteins, etc. in cells, tends to be accumulated. Recently, tools which may analyze various responses in cells, such as metabolic responses of chemical substances, signal transduction responses, etc. are developed and thus importance of cell modeling rises. Particularly, in the case of BioModels, it is reported that there are about 577 curated biomodels and about 722 biomodels in a previous step prior to curation, and the numbers of these biomodels tend to be increased.

Mathematical prediction of biomodels is executed through development of tools or programs which may simulate biomodels. In the initial stage of research, biomodels were mainly analyzed through metabolic pathway analysis and such analysis is executed based on tools to find the value of an ordinary differential equation, such as Gepasi, Gopasi, etc.

However, since most intracellular responses require understanding of more complicated regulation mechanisms as signal transduction pathways, analysis by the above-described method, research or tools is limited. Therefore, tools which may simulate signal transduction of cells including VCells, etc. have been developed. MCell, which may simulate actual intracellular responses in a 3D space of an actual cell differently from the conventional tools to find the value of the ordinary differential equation, has been developed, and CellBlender, which was recently developed, supports editing, design and visualization of biomodels. Further, Smoldyn, which was recently developed, may execute modeling of the 3D space of a cell, diffuse molecules in the cell through Brownian Motion, and simulate whether or not respective substances are stochastically bonded and react with each other using a probability model.

However, the above-described simulation tools or methods may execute only fragmentary simulation in which chemical reaction is caused based on initial conditions and equations and thus the aspect of a response until a specific time is measured, and have disadvantages, such as a impossibility of executing simulation throughout the life cycle of cells according to production and degradation of proteins, which are actually generated in the cells, and a difficulty in delicately analyzing mass movement between cellular organelles and cytoplasm and biochemical responses.

SUMMARY OF THE INVENTION

Accordingly, the present invention is directed to a simulation apparatus and method for intracellular responses that substantially obviate one or more problems due to limitations and disadvantages of the related art.

An object of the present invention is to provide a provide a 3D simulation apparatus and method in which intracellular responses throughout the life cycle of cells, not intracellular responses in a short period of time, may be 3-dimensionally simulated using gene expression information.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a simulation apparatus for intracellular responses includes a database configured to include information regarding cells for cell model generation, a model generation module configured to receive the information regarding cells from the database and to generate a cell model, an expression module configured to receive the information regarding cells from the database and to construct a numerical model for protein quantification, and a simulation module configured to allocate intracellular responses in the generated cell model to at least one computer and to simulate the intracellular responses, wherein the simulation module receives quantified amounts of the proteins from the expression module and executes simulation based on the received quantified amounts of the proteins.

In another aspect of the present invention, a simulation method for intracellular responses includes receiving information regarding cells for cell model generation from a database, generating a cell model based on the information regarding cells received from the database, constructing a numerical model for protein quantification based on the information regarding cells received from the database, and executing simulation by allocating cell responses in the generated cell model to at least one computer, wherein, in execution of simulation, quantified amounts of the proteins are received and simulation is executed based on the received quantified amounts of the proteins.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. In the following description of the present invention, a detailed description of known functions and configurations incorporated herein will be omitted when it may make the subject matter of the present invention rather unclear.

Figure 1:
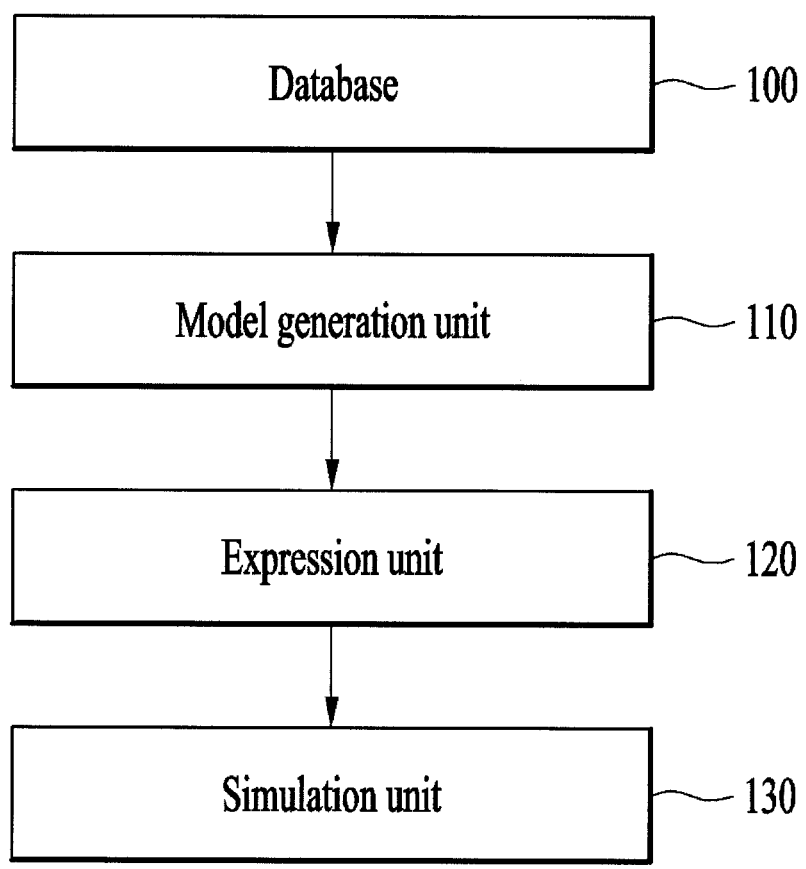
FIG. 1 is a block diagram of a module for illustrating an intracellular response simulation process in accordance with one embodiment of the present invention.

FIG. 1 is a block diagram of a module for illustrating an intracellular response simulation process in accordance with one embodiment of the present invention.

With reference to FIG. 1, a simulation apparatus for intracellular responses in accordance with one embodiment of the present invention may include a database 100, a model generation unit 110, an expression unit 120, and a simulation unit 130. Hereinafter, the respective elements will be described in detail.

The database 110 may include genomic information for cell model generation, protein information regarding the genomic information, cell structure information, intracellular biochemical response information, etc. The model generation unit 110 may receive the information for cell model generation from the database 110 and generate a 3D cell model to analyze and simulate intracellular responses. The expression unit 120 may provide intracellular expression information of genes to construct a numerical model for protein production. The simulation unit 130 may execute simulation in distributed environments as a function of simulating biological phenomena of the 3D cell model. That is, the simulation unit 130 may allocate an intracellular response to be analyzed to N computers and thus execute simulation. For the purpose of analysis of variance, M computing nodes which will execute simulation of intracellular organelles are allocated and mass movement at boundaries between cytoplasm and the organelles is executed through exchange of information between the computing nodes.

Figure 2:
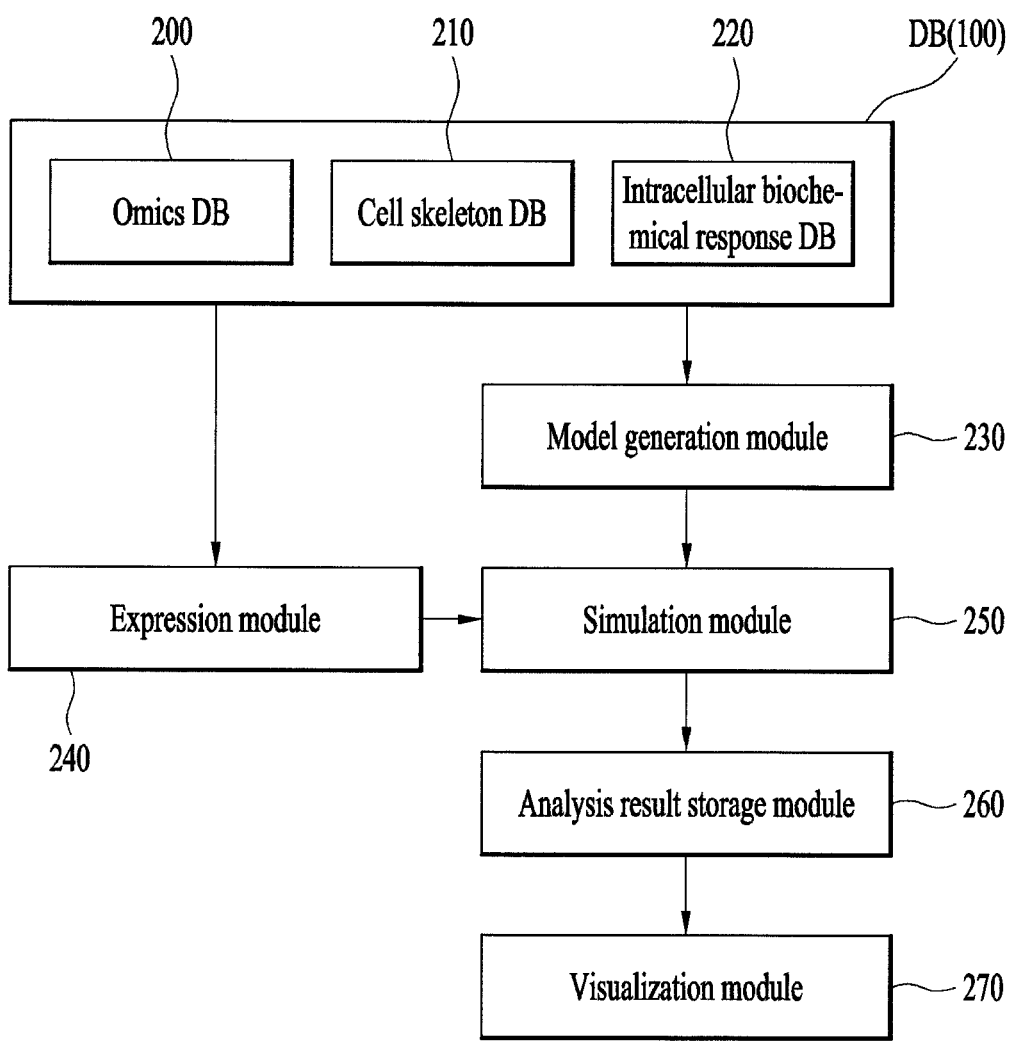
FIG. 2 is a view illustrating a simulation apparatus for intracellular responses in accordance with one embodiment of the present invention.

FIG. 2 is a view illustrating the configuration of a module to describe a simulation apparatus for intracellular responses in accordance with one embodiment of the present invention.

With reference to FIG. 2, in the intracellular response simulation process of the present invention, the above-described database 100 may include an omics database 200, a cytoskeleton database 210, and an intracellular biochemical response database 220. The omics database 200 may include genomic information of a living organism, protein information produced from the genomic information and information regarding overall substances constituting the living organism, such as various peptides, lipids, carbohydrates, ions, etc. The cytoskeleton database 210 may include information regarding cell structures constituting the living organism. In more detail, the cytoskeleton database 210 may include 3D structure information of intracellular organelles constituting a cell, such as a cell nucleus, mitochondria, endoplasmic reticulum, etc. The intracellular biochemical response database 220 may include various response pathways in cells known up to now and equations for intracellular responses.

A model generation module 230 may execute the function of the model generation unit 110, receive the information regarding substances constituting the living organism from the omics database 200, information regarding cell structures from the cytoskeleton database 210, and information regarding at least one biochemical response necessary for model generation from the intracellular biochemical response database 220, generate a cell model, and set the generated cell model as initial environments of simulation. In more detail, the model generation module 230 may receive 3D structure information regarding cells for cell model generation from the database 100, receive biochemical reaction information regarding the cells from the database 100, and then generate a cell model. An expression module 240 may execute the function of the expression unit 120, construct a numerical model for protein production, and provide the numerical model to a simulation module 250. The numerical model means quantification of expression information of respective proteins in time series. In more detail, the above-described numerical model means quantification of expression information of respective proteins, acquired from protein information through a micro-array, an RNA-seq experiment or a mass spectrometer, according to time. For this purpose, the expression module 240 may receive information from the database 100, measure expression amounts of proteins according to time through the above-described experiment, calculate necessary production amounts of the proteins according to time (in time series) and quantify the protein production amounts. Quantified information is converted into information of chemical reaction equations to produce proteins from genes and then the converted information is used in simulation. Further, the expression module 240 may transmit the quantified protein amounts to the simulation module 250 in real time so as to reflect the quantified protein amounts in simulation. Further, the expression module 240 may determine surroundings of a cell nucleus or a ribosome as a protein production space so as to be similar to a phenomenon in a living body. Further, individual protein objects generated by the expression module 240 may include response conditions. As an example of the response conditions, protease is used. In this case, protease plays a role of breaking down a specific protein in a cell and has a function of finally removing a protein object, generated from genes, from a 3D space in the cell. Through such a process, production and degradation of proteins may be dynamically implemented, and simulation under conditions similar to the conditions of an actual cell may be carried out. The expression module 240 may measure expression amounts of respective proteins in time series based on expression information of the respective proteins. The expression module 240 may calculate necessary production amounts of the respective proteins in time series based on the measured expression amounts and input the respective proteins, produced based on the calculated production amounts, to the simulation module 250 in real time. The respective produced proteins may include response conditions in that the proteins are degraded by protease.

The simulation module 250 may execute the function of the simulation unit 130. In more detail, in order to implement large-scale simulation for a long period of time, the simulation module 250 may execute simulation in distributed environments. Simulation in distributed environments means simulation in which computing for simulation is distributed to a plurality of computers. An intercellular response through particle-based simulation occurring when respective constituent substances in a cell collide is more similar to a biochemical response in an actual cell than a conventional numerical model in which an ordinary differential equation based chemical reaction equations is solved.

In order to implement such simulation, a 3D space in a cell is divided into cube-shaped 3D lattice structures to generate cell spaces. The simulation module 250 may allocate the respective 3D lattice structures to respective computer nodes so as to execute analysis. The simulation module 250 may allocate N cube spaces in the cell to be analyzed to nodes of a computer cluster and produce proteins in the 3D space based on information regarding an initial cell model to be simulated. The produced proteins move in the cell spaces through Brownian Motion, and cause biochemical responses if the proteins meet other proteins or substances and a desired condition is satisfied. Further, if there are constituent substances, such as proteins, compounds, etc., deviating from the 3D lattice spaces in the cell allocated to the respective computers, the simulation module 250 serving as a calculation node in charge of the 3D lattice spaces in the cell transmits the corresponding substances (proteins, compounds, etc.) deviating from the lattice spaces to a computer node executing corresponding simulation so that simulation may be continuously carried out. Further, in the case of a constituent substance produced by an intracellular organelle, the simulation module 250 may set a production position in the 3D cell space using initial position information of the corresponding constituent substance included in the database 100. For example, the simulation module 250 may execute simulation while restricting a membrane protein so as to move only within a membrane structure in the cell. Further, in order to implement simulation similar to an actual response in a cell, the simulation module 250 may execute simulation while continuously producing and degrading protein objects in the 3D cell space using information of respective protein objects produced by the expression module 240. Further, the simulation module 250 may simulate biochemical responses between each of the protein objects and substances with which each protein object moving in the cell space through Brownian Motion collides.

An analysis result storage module 260 may store information regarding movement pathways of respective substances over time in an intracellular 3D position space coordinate system, analyzed by the respective computers executing simulation. Further, the analysis result storage module 260 may store information substances which will be newly produced or degraded, if execution of a biochemical response by collision between two or more substances is determined. If a substance is newly produced, the analysis result storage module 260 may store object information regarding the newly produced substance and thereafter execute record of position information of the newly produced substance and tracking of biochemical responses of the newly produced substance with other substances, in the same manner as other objects. Since simulation is continuously executed, a file in which the above-described information is stored may be transmitted to a master node for storage in real time and all object information in the entire cell space may be managed in one file.

A visualization module 270 may execute visualization of the 3D cell space and structural spaces of intracellular organelles and visualization of position information of various intracellular compounds including proteins existing in the cell space. The visualization module 270 may read the intracellular object position information, simulated in time series, from the analysis result storage module 260 and display the read intracellular object position information in the 3D cell space. In order to visualize movement and chemical responses of the intracellular objects (proteins, compounds, etc.) according to time, the visualization module 270 visualizes movement of the respective objects so that a user may intuitively visually recognize position distribution of the objects in the cell and response situations of the objects.

Figure 3:
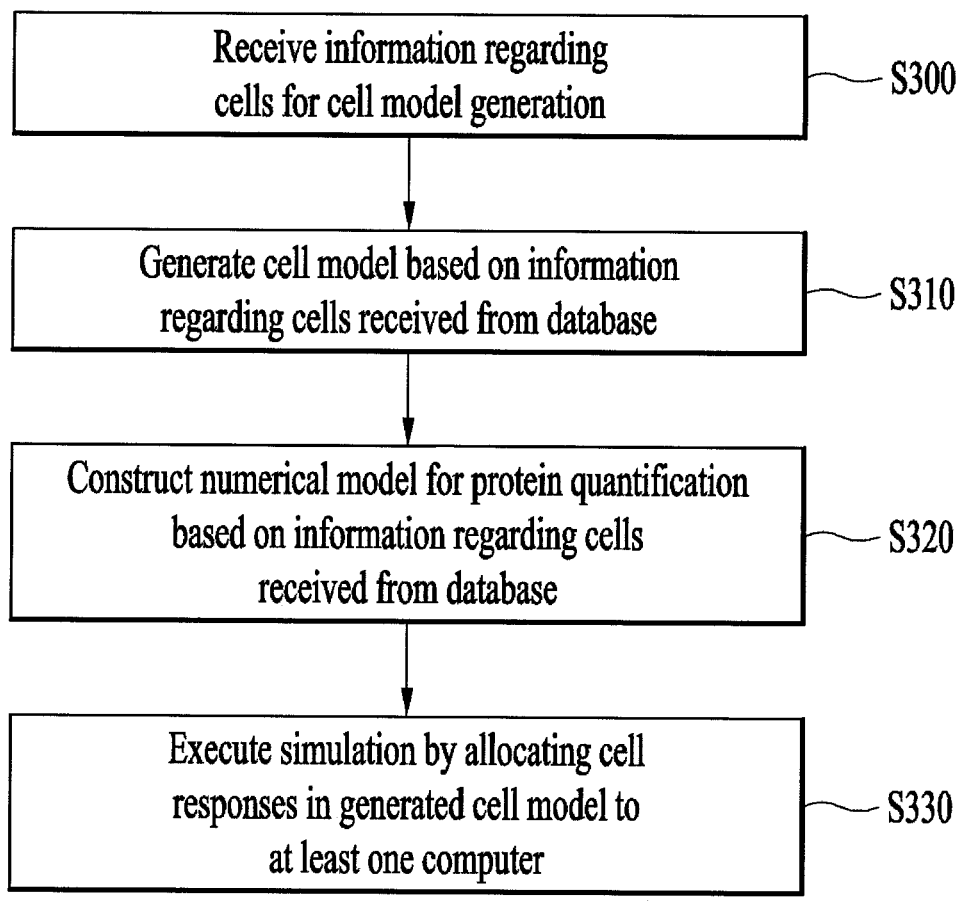
FIG. 3 is a flowchart illustrating a simulation method for intracellular responses in accordance with one embodiment of the present invention.

FIG. 3 is a flowchart illustrating a simulation method for intracellular responses in accordance with one embodiment of the present invention.

With reference to FIG. 3, the simulation method for intracellular responses of the present invention includes receiving information regarding cells for cell model generation from a database (Operation S300), generating a cell model based on the information regarding cells received from the database (Operation S310), constructing a numerical model for protein quantification based on the information regarding cells received from the database (Operation S320), and executing simulation by allocating cell responses in the generated cell model to at least one computer (Operation S330).

The database 100 may execute reception of the information regarding cells for cell model generation from the database (Operation S300). A detailed description thereof has been given above with reference to FIG. 2. The model generation module 230 may execute generation of the cell model based on the information regarding cells received from the database (Operation S310). A detailed description thereof has been given above with reference to FIG. 2. The expression module 240 may execute construction of the numerical model for protein quantification based on the information regarding cells received from the database (Operation S320). A detailed description thereof has been given above with reference to FIG. 2. The simulation module 250 may execute simulation by allocating cell responses in the generated cell model to at least one computer (Operation S330). A detailed description thereof has been given above with reference to FIG. 2.

As apparent from the above description, a simulation apparatus and method for intracellular responses in accordance with one embodiment of the present invention may execute simulation of various intracellular responses throughout the life cycle of cells for a long period of time based on protein expression information. Further, the simulation apparatus and method for intracellular responses may be used as an important technique which analyzes functions of cells and relations between signal transduction responses in the cells.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A simulation apparatus for intracellular responses, comprising:
    a database configured to include information regarding cells for cell model generation;
    a model generator configured to receive the information regarding the cells from the database and to generate a cell model;
    an expressor configured to receive the information regarding the cells from the database and to construct a numerical model for protein quantification;
    a simulator configured to allocate intracellular responses in the generated cell model to at least one computer and to simulate the intracellular responses, the simulator receiving quantified amounts of the proteins from the expressor and executing simulation based on the received quantified amounts of the proteins;

an analysis result storage module configured to store result information of the simulation analyzed by the at least one computer; and a visualization module configured to read the result information of the simulation from the analysis result storage module and to display the result information of the simulation in a 3D cell space such that position distribution for the cells is displayed to a user.

2. The simulation apparatus for the intracellular responses according to claim 1, wherein the database includes:

an omics database configured to include information regarding substances constituting a living organism;

a cytoskeleton database configured to include information regarding cell structures of the living organism; and an intracellular biochemical response database configured to include response equation information regarding the intracellular responses.

3. The simulation apparatus for the intracellular responses according to claim 1, wherein the numerical model quantifies respective proteins, acquired through a microarray or an RNA-seq experiment, according to time.

4. The simulation apparatus for the intracellular responses according to claim 1, wherein the simulator divides a cell space into cube-shaped 3D lattice spaces and then allocates the respective lattice spaces to the at least one computer so as to execute analysis.

5. The simulation apparatus for the intracellular responses according to claim 1, wherein, in order to implement the simulation similar to responses in an actual cell, the simulator executes the simulation while continuously producing and degrading proteins in a cell space based on information of the proteins generated by the expressor.

6. A simulation method for intracellular responses by a simulation apparatus for the intracellular responses, comprising:

receiving information regarding cells for cell model generation from a database;

generating a cell model based on the information regarding the cells received from the database;

constructing a numerical model for protein quantification based on the information regarding the cells received from the database;

executing simulation by allocating intracellular responses in the generated cell model to at least one computer, wherein, in execution of the simulation, quantified amounts of proteins are received and the simulation is executed based on the received quantified amounts of the proteins storing result information of the simulation analyzed by the at least one computer; and reading the result information of the simulation and displaying the result information of the simulation in a 3D cell space such that position distribution for the cells is displayed to a user.

7. The simulation method for the intracellular responses according to claim 6, wherein the database includes:

an omics database configured to include information regarding substances constituting a living organism;

a cytoskeleton database configured to include information regarding cell structures of the living organism; and an intracellular biochemical response database configured to include response equation information regarding the intracellular responses.

8. The simulation method for the intracellular responses according to claim 6, wherein the numerical model quantifies respective proteins, acquired through a microarray or an RNA-seq experiment, according to time.

9. The simulation method for the intracellular responses according to claim 6, wherein, in execution of the simulation, an intracellular space is divided into cube-shaped 3D lattice spaces and then the respective lattice spaces are allocated to the at least one computer so as to execute analysis.

10. The simulation method for the intracellular responses according to claim 6, wherein, in execution of the simulation, in order to implement the simulation similar to responses in an actual cell, the simulation is executed while continuously producing and degrading proteins in a cell space based on information of the proteins generated by an expressor.

11. A non-transitory computer readable storage medium of storing a simulation program for intracellular responses, the simulation program being configured to:

receive information regarding cells for cell model generation from a database;

generate a cell model based on the information regarding the cells received from the database;

construct a numerical model for protein quantification based on the information regarding the cells received from the database;

execute simulation by allocating intracellular responses in the generated cell model to at least one computer, wherein, in execution of the simulation, quantified amounts of the proteins are received and the simulation is executed based on the received quantified amounts of the proteins;

store result information of the simulation analyzed by the at least one computer; and read the result information of the simulation and display the result information of the simulation in a 3D cell space such that position distribution for the cells is displayed to a user.

12. The non-transitory computer readable storage medium according to claim 11, wherein the numerical model quantifies respective proteins, acquired through a microarray or an RNA-seq experiment, according to time.

13. The non-transitory computer readable storage medium according to claim 11, wherein, in execution of the simulation, an intracellular space is divided into cube-shaped 3D lattice spaces and then the respective lattice spaces are allocated to the at least one computer so as to execute analysis.

14. The non-transitory computer readable storage medium according to claim 11, wherein, in execution of the simulation, in order to implement the simulation similar to responses in an actual cell, the simulation is executed while continuously producing and degrading proteins in a cell space based on information of the proteins generated by an expressor.

* * * * *